United States Patent [19]

Saville

[11] Patent Number: Plant 7,058

[45] Date of Patent: Nov. 21, 1989

[54] MINIATURE ROSE PLANT NAMED SAVACHAS

[75] Inventor: F. Harmon Saville, Newburyport, Mass.

[73] Assignee: Nor'East Miniature Roses, Inc., Rowley, Mass.

[21] Appl. No.: 242,969

[22] Filed: Sep. 12, 1988

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new unusual bright yellow and red bicolor miniature rose.

1 Drawing Sheet

SUMMARY OF THE INVENTION

The present invention relates to a new and distinct variety of rose plant of the miniature rose class, which was originated by my crossing as seed parent the variety known as "Zorina" (U.S. Pat. No. P.P. 2,321) and as pollen parent the variety known as "Rainbow's End" (U.S. Pat. No. P.P. 5,482). The varietal denomination of this new rose is "Savachas".

Among the novel characteristics possessed by this new variety which distinguishes it from its parents and all other varieties of which I am aware are its unusual bright yellow and red bicolored flowers in this class of rose which are long lasting on the plant. Asexual reproduction by propagation by cuttings of the new variety as performed in San Bernardino County, Calif. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and as depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Color Chart (RHSCC). The terminology used in color description herein refers to plate numbers in the aforementioned color chart, e.g., "44B" is plate 44B of The Royal Horticultural Society Color Chart.

Parentage: Seedling.
*Seed parent.*—"Zorina".
*Pollen parent.*—"Rainbow's End".
Class: Miniature.

The following observations are made of specimens grown outdoors in San Bernardino County, Calif., during the month of April.

FLOWER

Blooming habit: Nearly continuous.

A. Bud:

(1) *Size.*—Small.
(2) *Form.*—Ovate.
(3) *Color.*—As sepals break and begin to divide, bud color is near 5A edged with near 44B to 45B.
(4) *Sepals.*—Relatively smooth, slightly longer than bud.
(5) *Peduncle.*—Length — about ½ inch. Aspect — straight. Strength — erect. Color — near 147D.

B. Bloom:
(1) *Size.*—Average size when fully expanded — about 1⅛ inch.
(2) *Borne.*—Singly, one to a stem and groups of 3 to 24 or more blooms
(3) *Form.*—High centered, exhibition style, at first, becoming flat. Outer petals reflex and quill to points; inner petals quill to points and roll under
(4) *Petalage.*—Number of petals under normal conditions — about 21
(5) *Color.*—After sepals fall and petals unfurl, beautiful brilliant yellow-coloring, near 13A to 13B, becomes visible. Viewing petals' top surface predominant color appears as near 15B to 13A to 13B, varying in color through this range but retaining color stability. Contrasting with the yellow is a red coloring, near 44B to 45A and B, at the edge and outer segments of some outer petals and on the reverse (under surface) of outer petals. Some minor washing or blending of the red into yellow occurs at the margin interface of these otherwise distinct color sections on those petals bearing both red and yellow coloration. The petal undersurface is predominantly yellow of a slightly lighter hut and some outer petals are imbued with strong red undertones and coloration. Overall tonality from a distance is brilliant yellow with bright red edging. Upon aging, the red coloration becomes more prominent. Color at point of petal attachment is near 12A.

C. Petals:
(1) *Texture.*—Thick.
(2) *Appearance.*—Inside velvety and outside satiny.
(3) *Form.*—Broad, fan shaped with pointed apices.
(4) *Arrangement.*—Regularly arranged, imbricated.
(5) *Petaloids in center.*—Few.
(6) *Persistence.*—Drop off cleanly.
(7) *Fragrance.*—Slight.
(8) *Lasting quality.*—Very long lasting on plant and long as cut flower.

REPRODUCTIVE ORGANS

A. Stamens, filaments and anthers:
*Arrangement and color.*—Regularly arranged around styles. Color — filaments near 15B.

B. Pollen:
*Color.*—Near 15D, but produces only little pollen.

C. Styles: Medium length, thin.

D. Stigmas:
*Color.*—Near 1C.

E. Hips: None observed.

PLANT

A. Form: Compact, well branched, symmetrical.

B. Growth: Very vigorous, uniform branching.
*Height attained.*—About 12 to 14 inches C. Foliage: Compound 5 to 7 leaflets.
(1) *Size.*—Small to medium.
(2) *Quantity.*—Abundant.
(3) *Color.*—New foliage: Upper side — near 137C. Under side — near 137D. Old foliage: Upper side — near 139A. Under side — between 139C and 139D.
(4) *Shape.*—Oval, pointed.
(5) *Texture.*—Upper side is semi glossy; under side is matte.
(6) *Edge.*—Serrate.

(7) *Serration.*—Ordinary but deeper toward leaflet tip.
(8) *Leaf stem.*—Color — Near 183C. Under side — Near 147C.
(9) *Stipules.*—Medium length, slightly bearded.
(10) *Resistance to disease.*—Blackspot — Average. Mildew — Average. Rust — Average.

D. Wood:
(1) *New wood.*—Color — Near 143C. Bark — Smooth.
(2) *Old wood.*—Color — Near 143A. Bark — Smooth.

E. Thorns:
(1) *Thorns.*—Quantity (main stalk) — ordinary. On laterls from stalk — few. Form — long, thin, curved slightly downward. Length — medium. Color — near 183D Position — irregular.
(2) *Bristles.*—None F. Winter hardiness: Needs protection in severe climates.

I claim:

1. A new and distinct variety of rose plant of the miniature rose class, substantially as shown and described, characterized particularly by attractive bright yellow and red bicolored flowers which are long lasting on the plant.

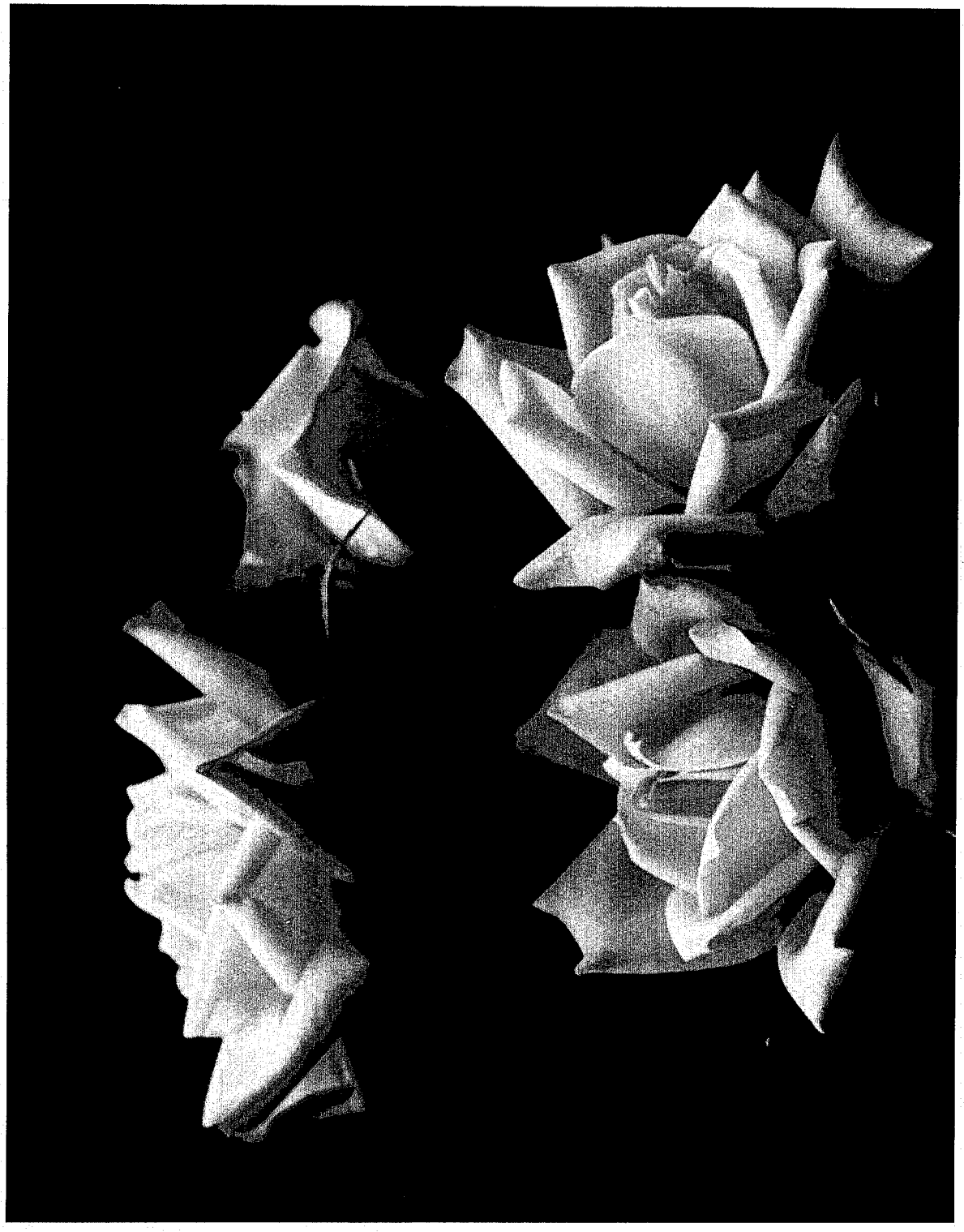

* * * * *